(12) United States Patent
Binder et al.

(10) Patent No.: US 6,794,175 B1
(45) Date of Patent: Sep. 21, 2004

(54) STRAIN OF EUBACTERIUM THAT DETOXYFIES TRICHOTHENES

(75) Inventors: Eva-Maria Binder, Tulln (AT); Johann Binder, Tulln (AT)

(73) Assignee: Erber Aktiengesellschaft, Herzogenberg (AT)

( * ) Notice: Subject to any disclaimer, the term of this patent is extended or adjusted under 35 U.S.C. 154(b) by 199 days.

(21) Appl. No.: 09/606,401

(22) Filed: Jun. 29, 2000

Related U.S. Application Data

(63) Continuation of application No. PCT/AT98/00316, filed on Dec. 21, 1998.

(30) Foreign Application Priority Data

Dec. 30, 1997 (AT) .............................................. 2204/97

(51) Int. Cl.$^7$ ................................................. C12N 1/20
(52) U.S. Cl. ................................ 435/252.1; 435/252.5; 435/34; 435/244
(58) Field of Search ........................... 435/252.1, 262.5, 435/34, 244

(56) References Cited

U.S. PATENT DOCUMENTS 5,478,557 A * 12/1995 Nisbet et al. ............. 424/93.21

FOREIGN PATENT DOCUMENTS

| AT | 000504 U1 | 12/1995 |
| DE | 4205196 A1 | 9/1992 |
| WO | WO91/13555 | 9/1991 |
| WO | WO92/05706 | 4/1992 |

OTHER PUBLICATIONS http://www.atcc.org/SearchCatalogs/Bacteria.cfm.*
J. Binder et al, Cereal Research Communications, vol. 25, No. 3, Part i, "Screening for deoxynivalenol . . . ", pp. 343–346, 1997.
Tokuo Matsushima et al, Journal of Gen. and Appl. Microbiology, vol. 42, No. 3, "Deacetylation of . . . ", pp. 225–234, 1996.
P. Boutibonnes, IRCS Medical Science, "Properties of a cell–line of bacillus thuringiensis . . . ", pp. 527–528, 1980.

* cited by examiner

*Primary Examiner*—Irene Marx
(74) *Attorney, Agent, or Firm*—Jacobson Holman PLLC

(57) ABSTRACT

Microorganism of the genus Eubacterium, and its obtainment and use, which is suitable in pure culture, DSM 11798, and/or mixed culture with the strain *Enterococcus casseliflavus*, DSM 11799, or in mixed culture with other anaerobic microorganisms for the detoxification of trichothecenes.

A feedstuff additive for the inactivation of trichothecenes in feedstuffs or in the digestive tract of animals contains a pure and/or mixed culture of the microorganism (DSM 11798 or DSM 11799) or a mixed culture with other anaerobic microorganisms in an amount from 0.2 to 3 kg, in particular 0.5 to 2.5 kg, per 1000 kg of feedstuff.

51 Claims, No Drawings

STRAIN OF EUBACTERIUM THAT DETOXYFIES TRICHOTHENES

The present application is a continuation application of PCT/AT98/00316, filed Dec. 21, 1998.

BACKGROUND OF THE INVENTION

1. Field of the Invention

The present invention relates to a microorganism of the genus Eubacterium, which is suitable in pure culture or mixed culture for the detoxification of trichothecenes, and to a process for the isolation thereof, its production and formulation and its use and a feedstuff additive comprising the microorganism.

2. Description of the Prior Art

Trichothecenes which belong to the mycotoxins class are contained in numerous animal feedstuffs, where they are customarily introduced into the feedstuffs via mould fungi found on cereals or grasses. As a result of the undesired administration of mycotoxins, in particular trichothecenes, to animals, both their productivity and, for example, the growth of the animals is inhibited, an increased consumption of feedstuff together with a simultaneously poorer feedstuff utilization rate occurring in addition to damage to the health of the animals. To eliminate the adverse effects of mycotoxins, numerous processes for binding or adsorbing these toxins have already been disclosed.

Thus, in WO 91/13555, for example, a feedstuff additive and a process for the inactivation of mycotoxins is described, where particles of a phyllosilicate mineral are added to the feed in order to inactivate the mycotoxins. To increase the effect of these phyllosilicates, the particles are coated with a sequestering agent in order to accelerate the effect. A feedstuff is furthermore known, for example, from WO 92/05706 in which montmorillonite clay is contained as a feedstuff additive. These natural clay minerals having large internal surface areas should bind the mycotoxins to the surface on account of their porosity and immobilize them in this manner.

Furthermore, a feedstuff additive has been disclosed in the Austrian Utility Model AT-U 504 in which an enzyme preparation is used which is capable of forming epoxidases and lactonases and degrading mycotoxins chemically both in the feedstuff and in the gastro-intestinal tract of animals. According to AT-U 504, the action of this enzyme preparation can be increased by the addition of zeolites and the like.

SUMMARY OF THE INVENTION

The present invention now aims at making available a specific microorganism or a defined mixed culture isolated from a natural habitat, with which it is possible to convert mycotoxins, in particular trichothecenes, in a controlled manner into substances which are physiologically harmless and which are harmless, in particular in animal breeding, by biochemical degradation.

To solve this object, a microorganism of the genus Eubacterium was isolated which is suitable for the detoxification of trichothecenes in pure culture, DSM 11798, or mixed culture with the strain *Enterococcus casseliflavus*, DSM 11799, or other anaerobic microorganisms. According to a novel refinement of the invention, the microorganism is suitable for the detoxification of trichothecenes in mixed culture with other anaerobic microorganisms, in particular from the genus Enterococcus, Streptococcus, Lactococcus, Bacillus or Lactobacillus.

The microorganism of the genus Eubacterium, which is also called Eubacterium sp. on account of its association with the genus Eubacterium, and which was deposited in pure culture in the Collection of German Microorganisms under the number DSM 11798, or in mixed culture with the strain *Enterococcus casseliflavus*, which was deposited in the Collection of German Microorganisms under the number DSM 11799, is in particular suitable according to the invention for the detoxification of, in particular, deoxynivalenol (DON), T-2 toxin, HT-2 toxin, nivalenol, monoacetoxyscirpenol, diacetoxyscirpenol, trichodermol, verrucarin, rorodin, acetyldeoxynivalenol, isotrichodermin, hydroxyisotrichodermin, calonectrin, T-2 tetraol, T-2 triol, deacetylneosolaniol, neosolaniol; acetylneosolaniol, sporotrichiol, trichotriol, sambucinol and culmorin. The microorganism according to the invention detoxifies the trichothecenes by reductive biotransformation of the epoxide group contained in the molecule, which epoxide group is responsible for the toxicity of the mycotoxins, in particular trichothecenes. In the trichothecenes corresponding to the following formula, the degradation of the epoxide group is carried out by reductive cleavage of the toxic 12,13-epoxy ring:

DSM 11798 and DSM 11799 were deposited with DSMZ-DEUTSCHE SAMMLUNG VON MIKROOGANISMEN UND ZELLKULTUREN GmbH, Mascheroder Weg 1b, D-38124 Braumschweig, Germany, on Sep. 17, 1997.

The morphology of the microorganism according to the invention shows preferably that it is an anaerobic gram-positive, rod-like, non-spore-forming bacterium, in particular 0.1 to 3 µm long, which occurs both individually, in pairs or in long chains, in particular up to approximately 150 µm. Phylogenetic analysis of the microorganism according to the invention has in particular shown a 16S RNA sequence, namely

```
  1 CCTGGCTCAG GATGAACGCT GGCGGCGTGC TTAACACATG CAAGTCGAAC GGATAACCCG

61 CCTCCGGGCG GTTATAGAGT GGCGAACGGG TGAGTAACAC GTGACCAACC TACCTCCCAC

121 TCCGGGATAA CCCAGGGAAA CCTGCGCTAA TACCGGATAC TCCGGGGCCC CCGCATGGGG
```

-continued

```
 181 GCGCCGGGAA AGCCCCGACG GTGGGAGATG GGGTCGCGGC CTATTAGGTA GTCGGCGGGG

241 TAACGGCCCA CCGAGCCCGC GATAGGTAGC CGGGTTGAGA GACCGATCGG CCACATTGGG

301 ACTGAGATAC GGCCCAGACT CCTACGGGAG GCAGCAGTGG GGAATTTTGC GCAATGGGGG

361 AAACCCTGAC GCAGCAACGC CGCGTGCGGG ACGAAGGCCT TCGGGTTGTA AACCGCTTTC

421 AGCAGGGAAG AAGTTGACGG TACCTGCAGA AGAAGCTCCG GCTAACTACG TGCCAGCAGC

481 CGCGGTAATA CGTAGGGAGC GAGCGTTATC CGGATTTATT GGGCGTAAAG CGCGCGTAGG

541 CGGGCGCTTA AGCGGAATCT CTAATCTGAG GGCTCAACCC CCAGCCGGAT TCCGAACTGG

601 GCGCCTCGAG TTCGGTAGAG GAAGACGGAA TTCCCAGTGT AGCGGTGAAA TGCGCAGATA

661 TTGGGAAGAA CACCGATGGC GAAGGCAGTC TTCTGGGCCG TAACTGACGC TGAGGTGCGA

721 AAGCTAGGGG AGCGAACAGG ATTAGATACC CTGGTAGTCC TAGCCGTAAA CGATGGGCAC

781 TAGGTGTGGG GGGGAATGCC CCTCCGTGCC GCAGCTAACG CATTAAGTGC CCCGCCTGGG

841 GAGTACGGCC GCAAGGCTAA AACTCAAAGG AATTGACGGG GGCCCGCACA AGCAGCGGAG

901 CATGTGGCTT AATTCGAAGC AACGCGAAGA ACCTTACCAG GGCTTGACAT GCAGGTGAAG

961 CGGCGGAAAC GCCGTGGCCG AGAGGAGCCT GCACAGGTGG TGCATGGCTG TCGTCAGCTC

1021 GTGTCGTGAG ATGTTGGGTT AAGTCCCGCA ACGAGCGCAA CCCCTGTCGT ATGTTGCCAT

1081 CATTCAGTTG GGGACTCGTA CGAGACTGCC GGCGTCAAGC CGGAGGAAGG TGGGGACGAC

1141 GTCAAGTCAT CATGCCCTTT ATGCCCTGGG CTGCACACGT GCTACAATGG CCGGTACAAC

1201 GGGCTGCGAG CCAGCGATGG CGAGCGAATC CCTCAAAACC GGTCCCAGTT CGGATCGGAG

1261 GCTGCAACCC GCCTCCGTGA AGTCGGAGTT GCTAGTAATC GCGGATCAGC ATGCCGCGGT

1321 GAATACGTTC CCGGGCCTTG TACACACCGC CCGTCACACC ACCCGAGTTG TCTGCACCCG

1381 AAGTCGACGG CCCAACCCGC GAGGGGGAG TCGCCGAAGG TGTGGGGAGT AAGGGGGGTG

1441 AAGTCGTAAC AAGGTAGCCG TACCGGAAGG TGCGGCT,
```

The sequence data of the microorganism being compared with known 16S RNA gene sequences of representative microorganisms which are part of the domain of bacteria. This comparison analysis showed the greatest correspondence to bacteria of the genus Eubacterium. However, it was not possible to find any gene sequence corresponding sufficiently to a known microorganism, from which it results that the microorganism according to the invention is a microorganism within the genus Eubacterium which has still not been isolated and classified to date. Physiological investigations, such as, for example, fermentation spectra, reduction of nitrate to nitrite, also clearly showed the association with the genus Eubacterium.

A further object of the present invention is to make available a process for obtaining both a pure culture of the microorganism DSM 11798 and its mixed culture with the strain *Enterococcus casseliflavus*, DSM 11799, and other anaerobic microorganisms, an optimization of yield both in the economical and in the quantitative respect being aimed at in particular.

To achieve this object, the process according to the invention is carried out in such a way that a mixed culture DSM 11799 is obtained from the microorganism and *Enterococcus casseliflavus* from bovine rumen by culturing or fermenting at least twice in dilution series and anaerobic culturing conditions. To obtain both the mixed culture and the pure culture of the microorganism according to the invention, culturing and/or fermenting in dilution series at least twice has proved favourable, since in this manner an ensured purity of the desired products and, in particular, a removal of interfering by-products or contaminations with undesired microorganisms can be achieved. To maintain the anaerobic conditions, the culturing and/or fermentation according to the invention was preferably performed in a gas atmosphere of $H_2$ and $CO_2$, the gas atmosphere having a ratio of $H_2:CO_2$ of 10:90 to 90:10, in particular approximately 80:20, being particularly preferably selected. For the growth of the microorganism according to the invention, anaerobic conditions with a low redox potential are important, it surprisingly only being possible to achieve a sufficiently rapid growth in the presence of $H_2$.

An even more rapid growth of the microorganism according to the invention can be achieved by carrying out the culturing and/or fermentation at an overpressure of 0.2 to 3 bar, in particular 0.5 to 1 bar, as this corresponds to a further preferred embodiment. It was possible to achieve further improved growth of the microorganism DSM 11798 according to the invention by preferably carrying out the culturing and/or fermentation at a temperature of 35 to 42° C., in particular approximately 37° C. The pH optimum for the culturing or fermentation in the process according to the invention was preferably a pH of between 6 and 8 and in particular between 7 and 7.5. Under these conditions, it is possible to obtain both a pure culture of the microorganism DSM 11798 and its mixed culture (DSM 11799) described above in as short a time as possible and using relatively few dilution series. Optimal results can be achieved with the process according to the invention by preferably carrying out the culturing and/or fermentation in a media preparation comprising components selected from: arginine, citrulline, peptone, yeast extract, fatty acid mixture(s), mineral solution(s), glucose, haemin solution, menadione, vitamin solution, trace elements and reducing agents.

The components contained in a media preparation are in this case partially exchangeable, it being possible, for example, by addition of glucose to achieve a shift of the equilibrium in the mixed culture in the direction of *Enterococcus casseliflavus* or corresponding other anaerobic microorganisms, it being possible to control the process specifically depending on the amount of glucose added. According to a particularly preferred aspect of the invention, at the start of the culturing and/or fermentation 0.1 to 0.5% by weight, in particular 0.2% by weight, of glucose is added. By addition of 0.1 to 0.5% by weight of glucose, the growth of *Enterococcus casseliflavus* is promoted at the start of the culturing and/or fermentation, which leads to a fall in the redox potential. By lowering the redox potential, optimum growth conditions for the microorganism according to the invention were created, so that, for example, chemicals, such as cysteine, in the media preparation can be dispensed with by means of a controlled addition of glucose.

In order to achieve the detoxification of mycotoxins, in particular trichothecenes, to other advantageous effect with the microorganisms and/or mixed culture according to the invention, enzyme preparation of the active, trichothecene-detoxifying microorganism and/or other anaerobic microorganisms can preferably also be added according to the invention.

To obtain a pure culture of the microorganism DSM 11798, the process according to the invention is preferably carried out such that the pure culture of the microorganism DMS 11798 is obtained from the culture or fermentation solution DSM 11799 by at least two further dilution series in the media preparation, in particular with addition of L-arginine as a growth stimulator. By carrying out two further dilution series in the media preparation from the culture or fermentation solution, the microorganism DMS 11798 can be obtained completely pure from the mixed culture with *Enterococcus casseliflavus*, the addition of the growth stimulator L-arginine advantageously shifting the equilibrium in the direction of the pure culture of the microorganism. In this connection, the growth of the bacterium according to the invention is promoted the higher the concentration of L-arginine.

In order to lower the redox potential of the media preparation further, a procedure is preferably used according to the invention in which, for the fermentation of the pure culture of the media preparation, 1 to 4% by weight of a reducing agent, in particular of a mixture of cysteine/sodium sulphide/sodium carbonate solution, is added. Particularly for reasons of economy, according to the invention the addition of the reducing agent is kept as low as possible, it having been shown in the course of comparison experiments that an increase in the concentration of the reducing agent beyond 4% by weight causes no further acceleration of the growth of the microorganism.

To obtain a storable finished product, the process according to the invention is preferably continued by working up the culture or fermentation solution by concentrating, in particular centrifuging or filtering and/or stabilization, in particular by freeze- or spray-drying or encapsulating. In this connection, for example, the culture or fermentation solution is concentrated in a first step by removing liquid by centrifuging or filtering, and/or carrying out the stabilization directly from the fermentation solution, preferably with addition of a filler or carrier material, such as aluminium silicates, kieselguhrs, carbohydrates, sugar alcohols, starches, milk and whey powder, protein hydrolysates, yeasts and PVPP. By addition of these carriers or fillers, it is possible in the following stabilization step, in particular the So freeze-drying, spray-drying, encapsulation of pelletization step, to obtain a solid product in which the pure culture of the microorganism DSM 11798 or its mixed culture with the strain *Enterococcus casseliflavus*, DSM 11799, or other anaerobic microorganisms, in particular from the genus Enterococcus, Streptococcus, Lactococcus, Bacillus or Lactobacillus, which are suitable for the detoxification of trichothecenes, is deposited directly on a carrier, as a result of which a particularly easily manageable and storable as well as metabolically favourable product is obtained. By depositing the microorganism or its mixed culture on a substance having a large internal surface area, such as argillaceous earths, aluminium silicates, zeolites and the like, the intended degradation according to the invention of trichothecenes is further facilitated, since these are bound physically to the substance having a large internal surface area, whereupon the biochemical attack with the microorganism according to the invention is distinctly facilitated.

According to the invention, the microorganism is further used in pure and/or mixed culture (DSM 11798, DSM 11799) for the production of a feedstuff additive. A particularly preferred use according to the invention essentially results in that the pure and/or mixed culture (DSM 11798 and DSM 11799) is employed as a freeze- or spray-dried and/or encapsulated or pelleted immobilizate, if appropriate with addition of a carrier material. Both the pure and/or mixed culture of the microorganism according to the invention and the spray-dried immobilizate can be used directly as a feedstuff additive, it even being possible to admix the feedstuff additive to the feedstuff directly during preparation and/or to mix it into the feedstuff either in solid or in liquid form during feeding to the animals.

In order to achieve an as complete as possible degradation or chemical conversion of the trichothecenes into physiologically acceptable substances, a feedstuff additive according to the invention for the inactivation of trichothecenes in feedstuffs or in the digestive tract of animals is essentially characterized in that the feedstuff additive contains a pure and/or mixed culture of a microorganism according to the invention or of a microorganism prepared according to the invention in an amount from $10^5$ to $10^{12}$ cells/kg, in particular $10^7$ to $10^9$ cells/kg, per 1000 kg of feedstuff. By use of $10^5$ to $10^{12}$ cells/kg, in particular $10^7$ to $10^9$ cells/kg, of the microorganism according to the invention or of the mixed culture according to the invention of the microorganism and *Enterococcus casseliflavus* or other anaerobic microorganisms, in particular of the genus Enterococcus, Streptococcus, Lactococcus, Bacillus or Lactobacillus, which are suitable for the detoxification of trichothecenes, it is possible to convert high concentrations of trichothecenes, in particular of deoxynivalenol, T-2 toxin, HT-2 toxin, nivalenol, monoacetoxyscirpenol, diacetoxyscirpenol, trichodermol, verrucarin, rorodin, acetyldeoxy-nivalenol, isotrichodermin, hydroxyisotrichodermin, calonectrin, T-2 tetraol, T-2 triol, deacetyl-neosolaniol, neosolaniol, acetylneosolaniol, sporotrichiol, trichotriol, sambucinol and culmorin in feedstuffs into chemically harmless substances, such as the deepoxy metabolite of deoxynivalenol (DOM-1), so that, using the feedstuff additive according to the invention, both an increase in productivity of the animals and, on account of the reduced toxicity, an improved feedstuff conversion rate can be achieved.

In order to further facilitate the biochemical degradation of the mycotoxins, in particular trichothecenes, according to the invention a carrier material and/or filler can preferably be additionally contained in the feedstuff additive in an amount of 0.5 to 8 kg/1000 kg, in particular 0.7 to 4 kg/1000 kg, of the feedstuff. By means of the addition of carrier materials and/or fillers, it is possible, if desired, to bind the mycotoxins and also other harmful substances to be degraded which can be contained in the feedstuff, physically to the substances, as a result of which they are no longer available for metabolization.

In this case, in particular, aluminium silicates, kieselguhrs, carbohydrates, sugar alcohols, starch, milk and whey powder, protein hydrolysates, yeasts and/or PVPP are employed as a carrier material and/or filler, these carrier materials and/or fillers having proved to be particularly advantageous for the binding of toxins, in particular trichotoxins.

A particularly preferred feedstuff additive is characterized in that the feedstuff additive consists of a mixture of 1 to 65% by weight, in particular 5 to 50% by weight, of the spray- or freeze-dried immobilizate of the microorganism and 99 to 35% by weight, in particular 95 to 50% by weight, of carrier material and/or filler. Feedstuff additives of this type are suitable, in particular, for the inactivation of deoxynivalenol (DON), T-2 toxin, HT-2 toxin, nivalenol, monoacetoxyscirpenol, diacetoxyscirpenol, trichodermol, verrucarin, rorodin, acetyldeoxy-nivalenol, isotrichodermin, hydroxyisotrichodermin, calonectrin, T-2 tetraol, T-2 triol, deacetyl-neosolaniol, neosolaniol, acetylneosolaniol, sporotrichiol, trichotriol, sambucinol and culmorin both in the feedstuff and in the digestive tract of animals.

DETAILED DESCRIPTION OF PREFERRED EMBODIMENTS OF THE INVENTION

The invention is further explained below by means of characterization of the microorganism according to the invention, its growth and activity conditions and the formation of metabolic products of trichothecenes with the aid of the microorganism according to the invention and by means of working examples of feeding tests.

The microorganism according to the invention is an active, trichothecene-transforming strain, in particular a deoxynivalenol-transforming strain, and is obtained from bovine rumen by repeated culture in an optimized nutrient medium under anaerobic culturing conditions, namely a $CO_2:H_2$ gas atmosphere (20/80 v/v) and an overpressure of 0.5 to 1.5 bar. PYG and PY media were used here as a media preparation, which in each case consisted of differing concentrations of two different mineral solutions, menadione stock solution, haemin solution, yeast extract, peptone, glucose being additionally added to the PYG medium. In order to lower the redox potential, 2 to 4% by weight of a reducing solution consisting of cysteine/$Na_2S$/$Na_2CO_3$ solution were added both to the PYG and the PY medium and the pH was adjusted to a value of 7 to 7.5 by $CO_2$ gassing. It is possible with the aid of this media preparation to obtain both a pure culture of the microorganism DSM 11798 by carrying out several dilution series, and also, in particular with the PYG medium, to obtain a mixed culture of the microorganism and *Enterococcus casseliflavus* (DSM 11799). The growth of the microorganism is exclusively achieved under strictly anaerobic conditions with a sufficiently low redox potential and the presence of $H_2$. The optimum growth of the microorganism can be achieved at approximately 37° C., it also being possible, however, to achieve adequate growth of the microorganism between 35° C. and 38° C. For culturing the pure culture of the microorganism DSM 11798, L-arginine in liquid medium has a stimulating effect.

Using the microorganism according to the invention, it is possible, in trichothecenes, to detoxify these by reductive cleavage of the toxic 12,13-epoxy ring.

The reaction scheme is subsequently, shown here with the aid of the trichothecenes generally and also the specific trichothecene deoxynivalenol.

Both the fermentation conditions and useable fermentation processes will subsequently be illustrated by way of example for the fermentation of the microorganism DSM 11798 according to the invention and in coculture with other facultative and anaerobic microorganisms and in mixed culture with *Enterococcus casseliflavus* (DSM 11799).

Fermentation conditions: Fermentation temperature between 35 and 42° C., in particular approximately 37° C.; pH range for the fermentation between 6 and 8, in particular 7.0–7.5; Redox potential: 0--350 mV, depending on how the process is carried out; Gas atmosphere: $H_2/CO_2$ 10:90 to 90:10, in particular 80:20; Fermentation pressure: 0.2–3 bar, in particular 0.5 to 1 bar.

Essential media constituents: arginine, citrulline, yeast extract, peptones, haemin and haemin-containing substances, lower fatty acids, mineral solution, carbonate buffer (sodium carbonate+$CO_2$), optionally glucose, trace element solution, vitamin solution and reducing agent.

Various ways of carrying out the fermentation process can be selected here

1) Batch Fermentation of the Pure Culture DSM 11798

Procedure: sterilization of the medium at 121° C. and 1.5 bar or sterile filtration. Cooling of the medium to fermentation temperature of 35–42° C., in particular 37° C., while gassing with sterilized $CO_2$ and addition of sodium carbonate and reducing agent. The gassing is continued until a pH of 6–8, in particular of 7–7.5, is achieved. Subsequent addition of 1–10% of inoculum which was precultured for 24–48 h, in particular 5%. Fermentation until the start of the stationary phase—duration approximately 20–50 h, depending on the substrate concentration or until a microorganism count in the range form $10^{13}$–$10^{16}$ is achieved.

The process is essentially controlled by the substrate concentration

2) Fed-batch Fermentation of the Pure Culture DSM 11798

Procedure: sterilization, buffering, reduction and inoculation of the medium as in 1. Increase in the biomass yield by means of batchwise or continuous addition of substrate, e.g. arginine, citrulline. The culture is kept in the exponential growth phase by keeping the substrate concentration at a relatively high level. A fermentation time of up to 60 h is possible using this method of carrying out the process.

The process is controlled by the substrate addition and fermentation time (accumulation of metabolic final products).

3) Continuous Fermentation of the Pure Culture DSM 11798

Procedure: sterilization, buffering, reduction and inoculation of the medium as in 1. Batch fermentation up to the start of the stationary phase then conversion to continuous fermentation by means of addition of sterile nutrient solution. The effluent is collected in a storage tank and worked up batchwise or continuously spray-dried.

4) Fermentation of the pure culture DSM 11798 in coculture with other facultati ve and strictly anaerobic microorganisms or fermentation of the coculture DSM 11799

| Examples of cocultures which can be employed: | |
| --- | --- |
| $H_2$ producers | DSM 11798 + Butyrvibrio sp. |
| | DSM 11798 + Ruminococcus sp. |
| Probiotics | DSM 11798 + Enterococcus casseliflavus = DSM 11799 |
| | DSM 11798 + Streptococcus sp. |
| | (enterococci, lactic acid |
| | streptococci, anaerobic streptococci) |
| | DSM 11798 + Leuconostoc sp. |
| | DSM 11798 + Pediococcus sp. |
| | DSM 11798 + Lactobacillus sp. |
| | DSM 11798 + Bifidobacterium sp. |
| | DSM 11798 + Bacillus sp. |
| | DSM 11798 + Megasphera sp. |
| Yeasts | DSM 11798 + Saccharomyces sp. |
| | DSM 11798 + Klyveromyces sp. |
| | DSM 11798 + Candida sp. |

Use of co-organisms in the fermentation serves on the one hand to reduce the redox potential in the fermentation, to produce hydrogen for DSM 11798 and as a protective organism in the work-up and stabilization. A minimization of microorganism count losses of DSM 11798 takes place here and they serve in some cases as additional productivity promoters in animal production.

4a) Batch Fermentation in Coculture

I) Preculturing of the co-organism on carbohydrate-containing medium. The medium described above, which, however, contains no reducing agent but additionally carbohydrates for this purpose, is used for reducing the redox potential. Subsequent inactivation of the coorganism and inoculation of DSM 11798.

II) Simultaneous inoculation of the co-organism and DSM 11798 and addition of 0.1–1% carbohydrate to the medium. The medium described above, which, however, contains no reducing agent but additionally carbohydrates for this purpose, is used. The growth of the co-organism is promoted—rapid fall in the redox potential—DSM 11798 begins to grow on account of the ideal growth conditions.

III) In combination with I+II: at the end of the fermentation addition of carbohydrates for refermentation of the co-organism. This leads to a protective effect (oxygen) in the work-up and stabilization on account of the increased biomass yield.

4b) Fed-batch Fermentation in Coculture

*) batch phase corresponding to 4aI, subsequently continuous/batchwise addition of substrate (arginine, citrulline) corresponding to 2.

**) batch phase corresponding to 4aI, subsequently continuous/batchwise addition of a substrate combination (arginine/carbohydrates or citrulline/carbo-hydrates).

4c) Continuous Fermentation of the Coculture

Batch phase corresponding to 4aI, subsequent conversion to continuous fermentation by means of addition of an arginine/carbohydrate- or citrulline/carbohydrate-containing nutrient solution. Work-up as in 3.

Work-up of the Fermentation Products

1) Concentration by membrane filtration processes (ultrafiltration, microfiltration) or centrifugation. Subsequent spray-drying or lyophilization with or without organic and/or inorganic carrier materials.

2) Direct spray-drying or lyophilization with or without organic and/or inorganic carrier materials.

3) Continuous spray-drying of the fermentation broth with or without organic and/or inorganic carrier materials.

4) Encapsulation or Pelletization in Combination with 1, 2 or 3.

To check the activity of the DON-biotransforming strain (DSM 11798) in the intestinal medium, an in vitro model using pig's intestine was developed.

In this connection, in a 1st experiment an in vitro model with intestinal contents in buffer with addition of lyophilizate was developed.

The small intestine and large intestine of a freshly slaughtered pig were kept under a $CO_2$ atmosphere. The emptying of the contents of the sections of anterior, median and posterior small intestine and large intestine into individual vessels was carried out under a $CO_2$ atmosphere.

20 ml of anaerobic buffer+1 g of intestinal content ($CO_2$ gassed) +DON were incubated at 37° C. under a $CO_2$ or $H_2/CO_2$ atmosphere.

It was found here that in the anterior section of the small intestine a markedly positive effect can be noted on addition of active lyophilizate. The fact is particularly significant here that the marked activity could also be detected under pure $CO_2$ gassing.

A 2nd in vitro experiment was carried out using complete pieces of pig's intestine with addition of active suspension.

Pieces of pig's intestine (anterior, median, posterior, large intestine, each 6–8 cm) were incubated for 24 h with 200 ppm of DON in anaerobic, reduced, preincubated buffer (30 ml) at 37° C.

This modified in vitro test variant has the advantage that the physiological condition of the intestine is scarcely affected, since immediately after slaughter the entire intestine is transported into the laboratory and pieces of desired length are tied off there. The pieces are then separated off and incubated in buffer solution with DON and active culture.

The results are clear. The deepoxidation of DON to DOM-1 can be achieved by means of the active culture. It is significant that this activity can be demonstrated in all sections of the intestine, the highest activity being particularly to be found in the anterior intestine. This is important insofar as the major part of the food absorption and thus also the release of the mycotoxins likewise takes place there.

The action of the microorganism according to the invention both in pure culture (DSM 11798) and in mixed culture of the microorganism and *Enterococcus casseliflavus* (DSM 11799) as well as other anaerobic microorganisms, in particular of the genus Enterococcus, Streptococcus, Lactococcus, Bacillus or Lactobacillus will be demonstrated subsequently with the aid of a laboratory protocol concerning chicken cell cultures and in feeding examples on pigs and chickens.

With the aid of a laboratory protocol using chicken cell cultures, it is shown for the microorganism that this is able to chemically degrade mycotoxins, in particular trichothecenes, and especially deoxynivalenol and T-2 toxin, in particular to reduce them and convert them into physiologically acceptable substances, in the case of deoxynivalenol into the deepoxymetabolite thereof, namely DOM-1.

To culture the chicken lymphocytes, the following conditions were adhered to:

| | |
|---|---|
| Cell numbers used: | $2 \times 10^6$ cells/ml |
| Stimulation: | ConA 5 µg/ml |
| Mycotoxins: | DON, DOM-1 and T2 toxin, |
| Concentration range: | DON: 10–0.08 µg/ml |
| | DOM-1: 232–1.81 µg/ml |
| | T2 toxin: 30–0.234 ng/ml |

Total incubation time: 44 hours, of which 16 hours labelling time during culturing in an incubator: 40° C., 5% $CO_2$, saturated water vapour atmosphere.

With the aid of a laboratory protocol using chicken lymphocyte cell cultures, it is shown for the active culture that this is able to biochemically degrade mycotoxins, in particular trichothecenes, in particular to reduce them, and to convert them into physiologically acceptable substances. This is shown in the following by way of example of DON and its deepoxymetabolite DOM-1:

Microscopic Checking of the Cell Culture

The cell culture containing the chicken lymphocytes was continuously microscopically checked during the culturing.
Checking After 20 Hours The unstimulated cells are thickly and uniformly distributed, the checks with ConA show powerful stimulation and pronounced proliferation foci.

DON: proliferation foci are seen in all concentration stages, it being remarkable, however, that in a concentration range of 10 µg/ml–0.625 µg/ml marked reductions of the proliferation foci are to be observed with increasing toxin concentration.

DOM: proliferation foci in all concentration stages without an apparent change in comparison with the control up to the highest concentration stage of 58 µg/ml.

This means that even after 20 hours a marked adverse effect on the cell activity in the toxin batch is present from a concentration of 0.625 µg/ml, while with the deepoxymetabolite itself no negative effects, on the cell culture were seen even at a concentration of 58 µg/ml. Checking after 28 and after 44 hours:

The control batches (unstimulated and ConA) are unchanged.

The action of the DON on the cell culture has additionally increased. In those series in which a change was found even after 20 hours, marked damage to the cells was seen.

Even after these incubation times, it was not possible to find any adverse effect on the cell activity even at a concentration of the deepoxymetabolite of 58 µg/ml.

In a second experiment, the action of a feedstuff additive according to the invention in a feedstuff comprising the mycotoxin deoxynivalenol in an amount of 450 ppb which was fed to weaned piglets, was investigated.

Animals

Piglets of the breed "Large White" and "Landrasse" were divided into negative comparison groups, positive comparison groups and test groups. The experiment started directly after weaning (age of the piglets 20 to 22 days); the productivity parameters of the animals were determined 14 days later.

Feed

A commercially available piglet starter was fed to the pigs 7 days after weaning, after which they received a commercially available piglet growth feed. The mycotoxin deoxynivalenol was mixed with a small aliquot of the feed in a concentration of 450 ppb (dissolved in ethanol) in order to introduce it into the feed of the positive comparison group and the test group. The feed was given ad libitum.

Dose of the feedstuff additive

A feedstuff additive was added to the feed of the test group in a dose of 1 kg/t. The feedstuff additive used was a mixed culture of the microorganism according to the invention with *Enterococcus casseliflavus* (DSM 11799), aluminium silicate being added to the mixed culture as a carrier.

Microorganism count: $4 \times 10^8$ cells/kg of finished feedstuff

Results

The results are summarized in Table 1, which shows the average growth in weight and the average feed conversion rate in this test, the negative comparison group being fed with feed comprising neither mycotoxin nor the microorganism according to the invention, the positive comparison group being fed with feed comprising only mycotoxin, and the test group being fed with feed comprising mycotoxin and microorganism according to the invention.

TABLE 1

| | Negative comparison group | Positive comparison group | Test group |
|---|---|---|---|
| Number of animals | 45 | 45 | 45 |
| Test period (d) | 14 | 14 | 14 |
| Weight increase/animal/day (g) | 154.0 | 126.2 | 153.2 |
| Feedstuff intake/animal/day | 247 | 226.3 | 246.5 |
| Losses (total) | 0 | 0 | 0 |
| FCR | 1.60 | 1.79 | 1.61 |

Discussion

It is evident from this test that the feedstuff additive was capable of compensating the adverse effect of the deoxynivalenol contamination on weaned piglets, and that the piglets which received both the mycotoxin and the feedstuff additive consumed essentially the same amounts of feedstuff as the negative comparison group and also showed an identical feed conversion rate (FCR). These results make it clear that it was almost completely possible to compensate the negative effect of deoxynivalenol by the mixed culture according to the invention (DSM 11799).

In a further test, the effect of the feedstuff additive according to the invention against contamination with trichothecenes was shown in a chick feed. The parameters used were the final weight, the feed intake and the feed conversion rate as well as the losses of chicks. The clinical symptoms were also recorded.

13

Animals

Chicks of the breed Cobb were investigated from the first day of life onwards. The test was carried out using three groups, comprising 10,700, 10,900 and 15,700 chicks. A specific chicken feed was administered ad libitum to the chicken.

Dose of the feedstuff additive: The feedstuff additive was contained in a dose of 1 kg/t of chick feed, only the test group receiving the feedstuff additive. The feedstuff additive employed was a pure culture of the microorganism (DSM 11798).

Microorganism count: $1 \times 10^9$ cells/kg of finished feed

Trichothecenes were administered in the feedstuff to the test group and the positive comparison group in a total amount of 750 ppb (500 ppb of DON and 250 ppb of T-2 toxin).

Results: The following table shows the productivity parameters of all three groups.

TABLE 2

|  | Positive comparison group | Negative comparison group | Test group |
|---|---|---|---|
| Number of animals | 10,700 | 10,900 | 15,700 |
| Mean final weight in kg | 1.806 | 1.91 | 1.92 |
| Mean feedstuff intake in kg | 3.161 | 2.729 | 2.722 |
| Feed conversion rate (FCR) | 1.75 | 1.43 | 1.42 |

TABLE 2-continued

|  | Positive comparison group | Negative comparison group | Test group |
|---|---|---|---|
| Losses | 205 (1.92%) | 175 (1.61%) | 248 (1.58%) |

Clinical Observations

Marked oral irritation was evident in many animals of the positive comparison group.

Discussion

Even in the present case, the feedstuff additive was capable of completely compensating the adverse effect of the trichothecenes on the poultry in relation to the productivity parameters and the clinical symptoms. Even in the case of the poultry, it is seen that chicks of the test group, which also received the microorganism DSM 11798 in addition to mycotoxins, even had a slightly higher mean final weight than the negative comparison group, and this with a slightly lower mean feedstuff intake, as a result of which somewhat improved productivity parameters result even in relation to the negative comparison group. On using the feedstuff additive according to the invention comprising the microorganism according to the invention, this shows that not only the adverse effect of the mycotoxins was compensated, but it was possible to achieve a further increase in productivity in the animals which received the microorganism DSM 11798.

What is claimed is:

1. A biologically pure culture of a strain of the genus Eubacterium, DSM 11798, for the detoxification of a trichothecene by reductive cleaving of the 12,13-epoxy ring thereof.

2. A composition comprising the biologically pure culture of claim 1, and further comprising a strain of *Enterococcus casseliflavus*.

3. A composition comprising the biologically pure culture of claim 1, and further comprising at least one anaerobic microorganism.

4. A composition comprising the biologically pure culture of claim 3, wherein the anaerobic microorganism belongs to the genus Enterococcus, Streptococcus, Lactococcus, Bacillus, or Lactobacillus.

5. The biologically pure culture of claim 1, wherein the trichothecene is deoxynivalenol, T-2 toxin, HT-2 toxin, nivalenol, monoacetoxyscirpenol, diacetoxyscirpenol, trichodermol, verrucarin, rorodin, acetyldeoxynivalenol, isotrichodermin, hydroxyisotrichodermin, calonectrin, T-2 tetraol, T-2 triol, deacetylneosolaniol, neosolaniol, acetylneosolaniol, sporotrichiol, trichotriol, sambucinol, or culmorin.

6. The biologically pure culture of claim 1, wherein the culture detoxifies the trichothecene by reductive biotransformation of the epoxide group of the trichothecene.

7. The biologically pure culture of claim 1, wherein the strain of Eubacterium contains a 16S RNA sequence having SEQ ID NO:1.

8. The biologically pure culture of claim 1, wherein the culture is obtained by culturing DSM 11799, which is a mixed culture of a strain of *Enterococcus casselifavus* and DSM 11798 from bovine rumen, at least twice in dilution series in a media preparation under anaerobic conditions.

9. The biologically pure culture of claim 8, wherein the anaerobic conditions comprise a gas atmosphere of $H_2$ and $CO_2$.

10. The biologically pure culture of claim 9, wherein the gas atmosphere comprises a ratio of $H_2$:$CO_2$ in the range of 10:90 to 90:10.

11. The biologically pure culture of claim 10, wherein the gas atmosphere comprises a ratio of $H_2$:$CO_2$ of about 80:20.

12. The biologically pure culture of claim 8, wherein the anaerobic conditions comprise an atmospheric pressure of 0.2 to 3.0 bar.

13. The biologically pure culture of claim 12, wherein the atmospheric pressure is 0.5 to 1.0 bar.

14. The biologically pure culture of claim 8, wherein the anaerobic conditions comprise a temperature of 35 to 42° C.

15. The biologically pure culture of claim 14, wherein the temperature is 37° C.

16. The biologically pure culture of claim 8, wherein the anaerobic conditions comprise a pH between 6 and 8.

17. The biologically pure culture of claim 16, wherein the pH is between 7 and 7.5.

18. The biologically pure culture of claim 8, wherein the media preparation comprises arginine, citrulline, a peptone, a yeast extract, a fatty acid, a mineral, glucose, haemin solution, menadione, a vitamin, a trace element, reducing agent, or a combination thereof.

19. The biologically pure culture of claim 8, wherein 0.1 to 0.5% by weight of glucose is added at the start of the culturing.

20. The biologically pure culture of claim 8, wherein 0.2% by weight of glucose is added at the start of the culturing.

21. A composition comprising the biologically pure culture of claim 1, and further comprising an enzyme preparation of DSM 11799, an enzyme preparation of a strain of *Enterococcus casseliflavus*, an enzyme preparation of an anaerobic micoorganism, or a combination thereof.

22. The biologically pure culture of claim 8, wherein the culture is obtained by at least two further dilution series and adding L-arginine.

23. The biologically pure culture of claim 8, wherein 1 to 4% by weight of a reducing agent is added.

24. The biologically pure culture of claim 23, wherein the reducing agent is a mixture of cysteine/sodium sulphide/sodium carbonate in solution.

25. The biologically pure culture of claim 1, wherein the culture is concentrated, stabilized, or both.

26. The biologically pure culture of claim 25, wherein the culture is concentrated by centrifugation or filtration.

27. A biologically pure culture comprising a microorganism of the genus Eubacterium for the detoxification of a trichothecene by reductive cleaving of the 12,13-epoxy ring, thereof.

28. The biologically pure culture of claim 25, wherein the culture is stabilized by adding a filler or a carrier material.

29. The biologically pure culture of claim 28, wherein the filler or the carrier material is selected from the group consisting of aluminium silicates, kieselguhrs, carbohydrates, sugar alcohols, starches, milk powder, whey powder, protein hydrolysates, yeasts, and polyvinylpyrolidone.

30. A process of making a composition comprising the biologically pure culture of claim 1, comprising culturing DSM 11799, which is a mixed culture of *Enterococcus casselifavus* and DSM 11798 from bovine rumen, at least twice in dilution series in a media preparation under anaerobic conditions.

31. The process of claim 30, wherein the anaerobic conditions comprise a gas atmosphere of $H_2$ and $CO_2$.

32. The process of claim 31, wherein the gas atmosphere comprises a ratio of $H_2:CO_2$ in the range of 10:90 to 90:10.

33. The process of claim 32, wherein the gas atmosphere comprises a ratio of $H_2:CO_2$ of about 80:20.

34. The process of claim 30, wherein the anaerobic conditions comprise an atmospheric pressure of 0.2 to 3.0 bar.

35. The process of claim 30, wherein the atmospheric pressure is 0.5 to 1.0 bar.

36. The process of claim 30, wherein the anaerobic conditions comprise a temperature of 35 to 42° C.

37. The process of claim 36, wherein the temperature is 37° C.

38. The process of claim 30, wherein the anaerobic conditions comprise a pH between 6 and 8.

39. The process of claim 38, wherein the pH is between 7 and 7.5.

40. The process of claim 30, wherein the media preparation comprises arginine, citrulline, a peptone, a yeast extract, a fatty acid, a mineral, glucose, haemin solution, menadione, a vitamin, a trace element, reducing agent, or a combination thereof.

41. The process of claim 30, further comprising adding 0.1 to 0.5% by weight of glucose at the start of the culturing.

42. The process of claim 30, further comprising adding 0.2% by weight of glucose at the start of the culturing.

43. The process of claim 30, further comprising adding an enzyme preparation of DSM 11799, an enzyme preparation of a strain of *Enterococcus casseliflavus*, an enzyme preparation of an anaerobic micoorganism, or a combination thereof to the culture.

44. The process of claim 30, further comprising at least two further dilution series and adding L-arginine.

45. The process of claim 30, further comprising adding 1 to 4% by weight of a reducing agent.

46. The process of claim 45, wherein the reducing agent is a mixture of cysteine/sodium sulphide/sodium carbonate in solution.

47. The process of claim 30, further comprising concentrating and/or stabilizing the culture.

48. The process of claim 47, wherein the step of concentrating is carried out by centrifuging or filtering.

49. The process of claim 47, wherein the step of stabilizing is carried out by freeze-drying, spray-drying, or encapsulating.

50. The process of claim 47, wherein the step of stabilizing is carried out by adding a filler or a carrier material.

51. The process of claim 50, wherein the filler or the carrier material is selected from the group consisting of aluminium silicates, kieselguhrs, carbohydrates, sugar alcohols, starches, milk powder, whey powder, protein hydrolysates, yeasts, and polyvinylpyrolidone.

* * * * *

SEQUENCE LISTING

```
<160> NUMBER OF SEQ ID NOS: 1

<210> SEQ ID NO 1
<211> LENGTH: 1477
<212> TYPE: DNA
<213> ORGANISM: Eubacterium sp.

<400> SEQUENCE: 1
cctggctcag gatgaacgct ggcggcgtgc ttaacacatg caagtcgaac ggataacccg      60
cctccgggcg gttatagagt ggcgaacggg tgagtaacac gtgaccaacc tacctcccac     120
tccgggataa cccagggaaa cctgcgctaa taccggatac tccggggccc ccgcatgggg     180
gcgccgggaa agccccgacg gtgggagatg gggtcgcggc ctattaggta gtcggcgggg     240
taacggccca ccgagcccgc gataggtagc cgggttgaga gaccgatcgg ccacattggg     300
actgagatac ggcccagact cctacgggag gcagcagtgg ggaattttgc gcaatggggg     360
aaaccctgac gcagcaacgc cgcgtgcggg acgaaggcct tcgggttgta aaccgctttc     420
agcagggaag aagttgacgg tacctgcaga agaagctccg gctaactacg tgccagcagc     480
cgcggtaata cgtagggagc gagcgttatc cggatttatt gggcgtaaag cgcgcgtagg     540
cgggcgctta agcggaatct ctaatctgag ggctcaaccc cagccggat tccgaactgg      600 gcgcctcgag ttcggtagag gaagacgaa ttcccagtgt agcggtgaaa tgcgcagata     660
ttgggaagaa caccgatggc gaaggcagtc ttctgggccg taactgacgc tgaggtgcga     720
aagctagggg agcgaacagg attagatacc ctggtagtcc tagccgtaaa cgatgggcac     780
taggtgtggg ggggaatgcc cctccgtgcc gcagctaacg cattaagtgc cccgcctggg     840
gagtacggcc gcaaggctaa aactcaaagg aattgacggg ggcccgcaca agcagcggag     900
```

```
catgtggctt aattcgaagc aacgcgaaga accttaccag ggcttgacat gcaggtgaag      960
cggcggaaac gccgtggccg agaggagcct gcacaggtgg tgcatggctg tcgtcagctc     1020
gtgtcgtgag atgttgggtt aagtcccgca acgagcgcaa ccccctgtcgt atgttgccat    1080 cattcagttg gggactcgta cgagactgcc ggcgtcaagc cggaggaagg tggggacgac    1140
gtcaagtcat catgcccttt atgccctggg ctgcacacgt gctacaatgg ccggtacaac    1200
gggctgcgag ccagcgatgg cgagcgaatc cctcaaaacc ggtcccagtt cggatcggag    1260
gctgcaaccc gcctccgtga agtcggagtt gctagtaatc gcggatcagc atgccgcggt    1320
gaatacgttc ccgggccttg tacacaccgc ccgtcacacc acccgagttg tctgcacccg    1380
aagtcgacgg cccaacccgc gagggggag tcgccgaagg tgtggggagt aaggggggtg     1440
aagtcgtaac aaggtagccg taccggaagg tgcggct                              1477
```